(12) United States Patent
Lee

(10) Patent No.: US 10,509,019 B2
(45) Date of Patent: Dec. 17, 2019

(54) METHOD FOR DETERMINING SOIL MOISTURE

(71) Applicant: Hou Kuan Lee, New Taipei (TW)

(72) Inventor: Hou Kuan Lee, New Taipei (TW)

( * ) Notice: Subject to any disclaimer, the term of this patent is extended or adjusted under 35 U.S.C. 154(b) by 120 days.

(21) Appl. No.: 15/869,082

(22) Filed: Jan. 12, 2018

(65) Prior Publication Data

US 2019/0219557 A1 Jul. 18, 2019

(51) Int. Cl.
*G01N 33/24* (2006.01)
*G01N 27/04* (2006.01)

(52) U.S. Cl.
CPC ......... *G01N 33/246* (2013.01); *G01N 27/048* (2013.01)

(58) Field of Classification Search
CPC .............................. G01N 33/246; G01N 27/48
See application file for complete search history.

(56) References Cited

U.S. PATENT DOCUMENTS

| | | | |
|---|---|---|---|
| 7,239,150 B2 * | 7/2007 | Troxler | G01N 22/00 324/634 |
| 2004/0201385 A1 * | 10/2004 | Drnevich | G01N 33/246 324/643 |
| 2018/0224382 A1 * | 8/2018 | Golombek | G01N 33/246 |
| 2018/0239044 A1 * | 8/2018 | Rhodes | G01V 3/088 |

* cited by examiner

*Primary Examiner* — Dominic E Hawkins
(74) *Attorney, Agent, or Firm* — Leong C. Lei

(57) ABSTRACT

The method for determining soil moisture includes the following steps: measuring an initial electrical conductivity and an initial dielectric constant of a training sample of a soil, adjusting the training sample's water content by adding a fixed amount of water and obtaining a plurality of adjusted electrical conductivities and dielectric constants from the adjusted training sample, entering the initial and adjusted electrical conductivities and dielectric constants into a computing device, obtaining a regression value from the initial and adjusted electrical conductivities and dielectric constants of the training sample, measuring a final electrical conductivity and a final dielectric constant from a real sample of the soil, and determining the soil moisture of the soil using the regression value and the final electrical conductivity and dielectric constant of the real sample.

7 Claims, 8 Drawing Sheets

METHOD FOR DETERMINING SOIL MOISTURE

BACKGROUND OF THE INVENTION

(a) Technical Field of the Invention

The present invention is generally related to the measurement of soil properties, and more particular to a method for determining soil moisture.

(b) Description of the Prior Art

To intelligently control soil moisture, there are various methods for determining soil moisture such as Time Domain Reflectometry (TDR) and Frequency Domain Reflect Reflectometry (FDR).

Soil includes particles, air, and water. Air has a dielectric constant around 1, and water's dielectric constant is about 80. Therefore, soil's dielectric constant usually varies between 1 and 81 depending on its water content. Actual experiments however reveal that, when soil's real water content reaches a certain amount, a determined soil moisture using conventional methods would deviate from its true soil moisture, and the discrepancy would increase as there is more water content in the soil.

For example, the soil dielectric constant K based on the FDR methods has the following equation: $K=K'-i(K''+\sigma_{dc}/2\pi f\varepsilon_0)$, where $K'$ and $K''$ are the real part and imaginary part of the dielectric constant K, $\sigma_{dc}$ is the electrical conductivity (EC), $\varepsilon_0=8.85\times10^{-12}$ $m^{-3}kg^{-1}s^4A^2$ is the dielectric constant in vacuum, and f is the frequency of simulation signal. Therefore, there would be some significant error when $\sigma_{dc}$ is great.

The commonly used Topp Equation specifies that $\theta_v=-5.3\times10^{-2}+2.92\times10^{-2}\times\varepsilon-5.5\times10^{-4}\times\varepsilon^2+4.3\times10^{-6}\times\varepsilon^3$, where $\theta_v$ is the volumetric soil moisture and $\varepsilon$ is the real part of the dielectric constant K. The soil moisture therefore may be estimated using Topp Equation and the real part of the soil's dielectric constant K when the soil is completely not conductive. But usually load cannot have zero conductivity (e.g., fertilizer would increase its conductively), Topp Equation therefore cannot be directly applied.

To see the relationship between the soil's dielectric constant (K) and electrical conductivity (EC), solutions of different NaCl concentrations are added to soils having 1:5 soil to water ratio to alter their ECs and corresponding dielectric constants are measured. As shown in the following table, eight soils of different ECs are measured, and the measured dielectric constants are plotted in FIG. 8.

|          | Soil # |     |     |     |     |     |     |     |
|----------|--------|-----|-----|-----|-----|-----|-----|-----|
|          | 1      | 2   | 3   | 4   | 5   | 6   | 7   | 8   |
| EC (dS/m) | 0.3   | 0.6 | 1.3 | 1.7 | 2.3 | 3.4 | 4.9 | 6.3 |

A regression curve between EC and K then can be obtained from the above diagram as $K=78.19+1.88\times EC(dS/m)+0.35\times(EC(dS/m)-2.6)^2$.

Then the soil moistures for these soils of different ECs may be estimated by the Topp Equation as follows.

|                         | EC (dS/m) |       |      |       |       |      |       |       |
|-------------------------|-----------|-------|------|-------|-------|------|-------|-------|
|                         | 0.3       | 0.6   | 1.3  | 1.7   | 2.3   | 3.4  | 4.9   | 6.3   |
| Measured K (mean)       | 81.2      | 81.25 | 81.3 | 81.65 | 82.37 | 84.5 | 89.13 | 95.23 |
| $\theta_v$ from Topp Equation (%) | 99.4 | 99.5 | 99.8 | 101 | 102 | 108 | 122 | 145 |
| Error (%)               | 0         | 0     | 0    | 1     | 2     | 8    | 22    | 45    |

As shown in the above table, the error would be greater when EC is higher, and the error begins to emerge when EC is higher than 1.3 dS/m and would rise up to 45% (when EC=6.3 dS/m).

SUMMARY OF THE INVENTION

Therefore a major objective the present invention is to provide a method to improve the accuracy in determining soil moisture.

To achieve the objective, the method includes the following steps: measuring an initial electrical conductivity and an initial dielectric constant of a training sample of a soil, adjusting the training sample's water content by adding a fixed amount of water and obtaining a plurality of adjusted electrical conductivities and dielectric constants from the adjusted training sample, entering the initial and adjusted electrical conductivities and dielectric constants into a computing device, obtaining a regression value from the initial and adjusted electrical conductivities and dielectric constants of the training sample, measuring a final electrical conductivity and a final dielectric constant from a real sample of the soil, and determining the soil moisture of the soil using the regression value and the final electrical conductivity and dielectric constant of the real sample.

Through the above method, the prior art's problem of having greater error with more water content is effectively resolved.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
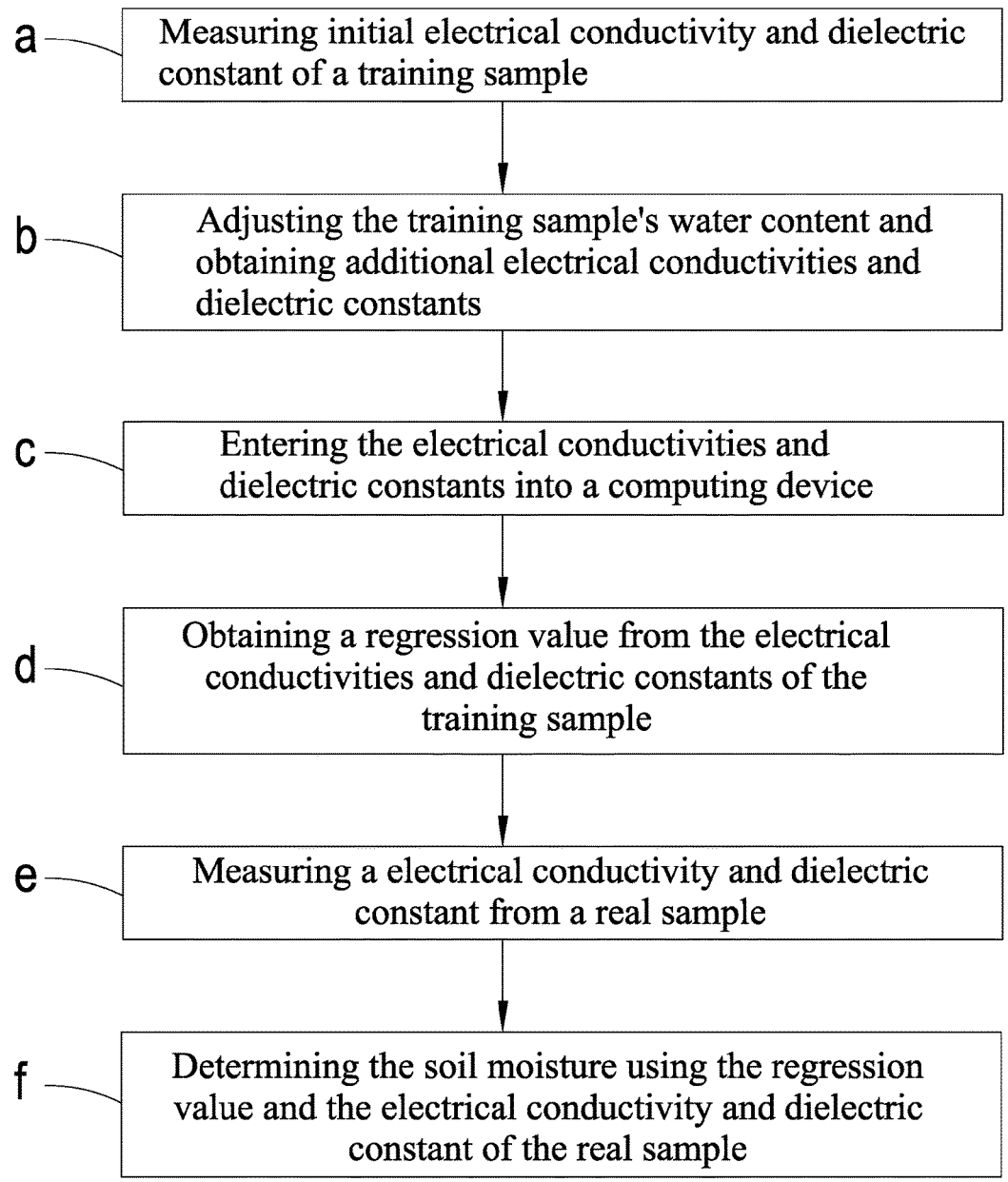
FIG. 1 is a flow diagram showing the steps of a method for determining soil moisture according to an embodiment of the present invention.

As shown in FIG. 1, a method for determining soil moisture according to an embodiment of the present invention includes the following steps: (a) measuring an initial electrical conductivity and an initial dielectric constant of a training sample of a soil, (b) adjusting the training sample's water content and obtaining a number of electrical conductivities and dielectric constants from the adjusted training sample, (c) entering the measured electrical conductivities and dielectric constants into a computing device, (d) obtaining a regression value from the measured electrical conductivities and dielectric constants of the training sample, (e) measuring an electrical conductivity and dielectric constant from a real sample of the soil, and (f) determining the soil moisture of the soil using the regression value and the measured electrical conductivity and dielectric constant of the real sample.

The step (a) includes the following sub-steps. The sub-step (a1) obtains a fixed volume of the soil as the training sample of the soil. The soil includes at least one of sandy soil, loam, clay soil, peat soil, peat moss, organic cultural soil, coconut bran, peat, coconut peat, coconut soil, cultural soil for cuttage propagation, field soil, easy transplanting soil, coir soil, coir brick, or coconut fiber soil. In the following, five training samples of soils of different combinations are tested to demonstrate the method of the present invention, as outlined in the following table.

| Sample# | Sandy soil % | Loam % | Clay soil % | Specific weight (g/cm$^3$) |
| --- | --- | --- | --- | --- |
| Soil1 | 95 | 5 | 0 | 1.5 |
| Soil2 | 95 | 14 | 21 | 1.4 |
| Soil3 | 9 | 21 | 70 | 1.2 |
| Soil4 | 6 | 79 | 15 | 1.2 |
| Soil5 | 46 | 26 | 28 | 1.4 |

Figure 2:
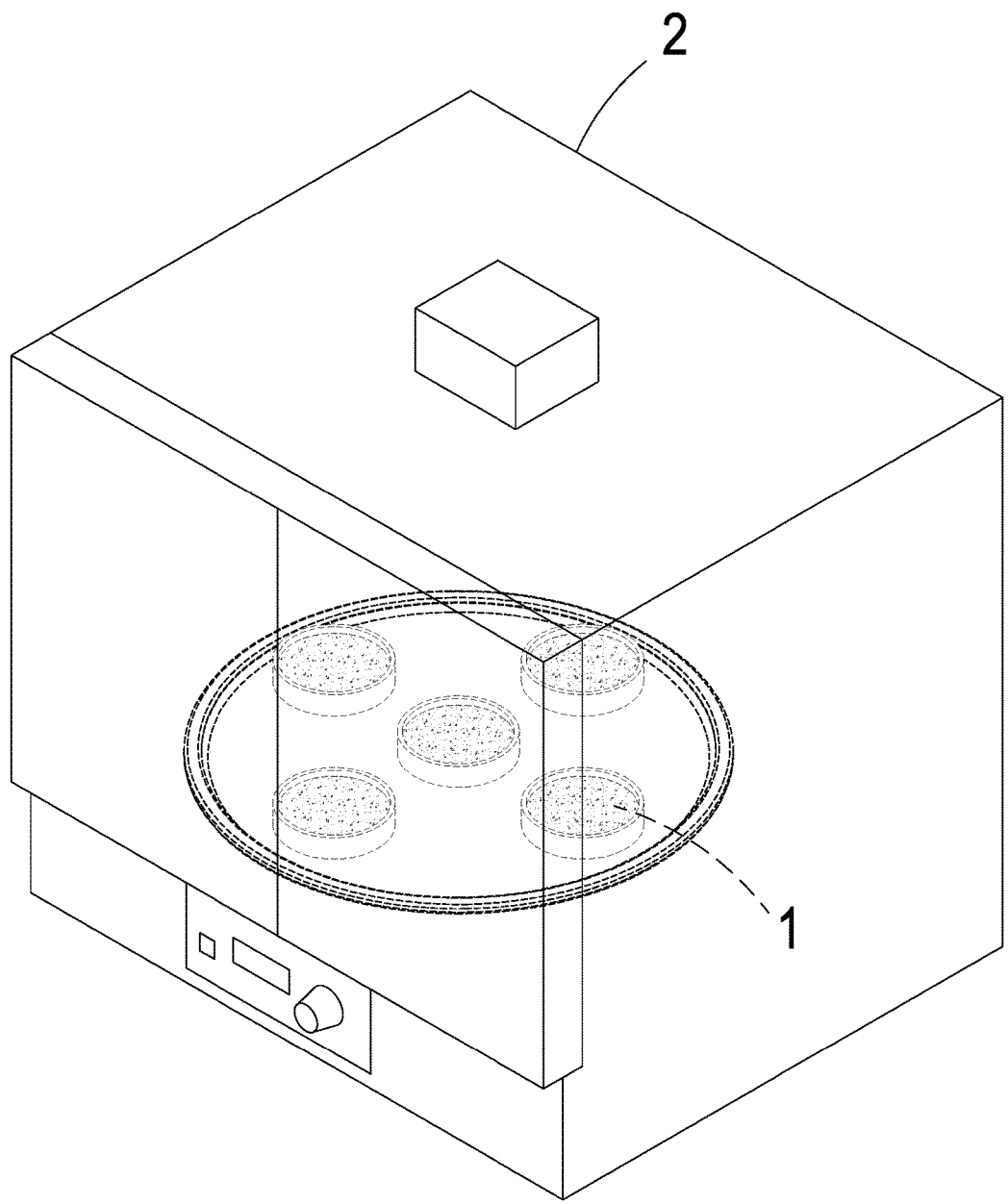
FIG. 2 is a schematic diagram showing how soil samples are dried according to the method of FIG. 1.
Figure 3:
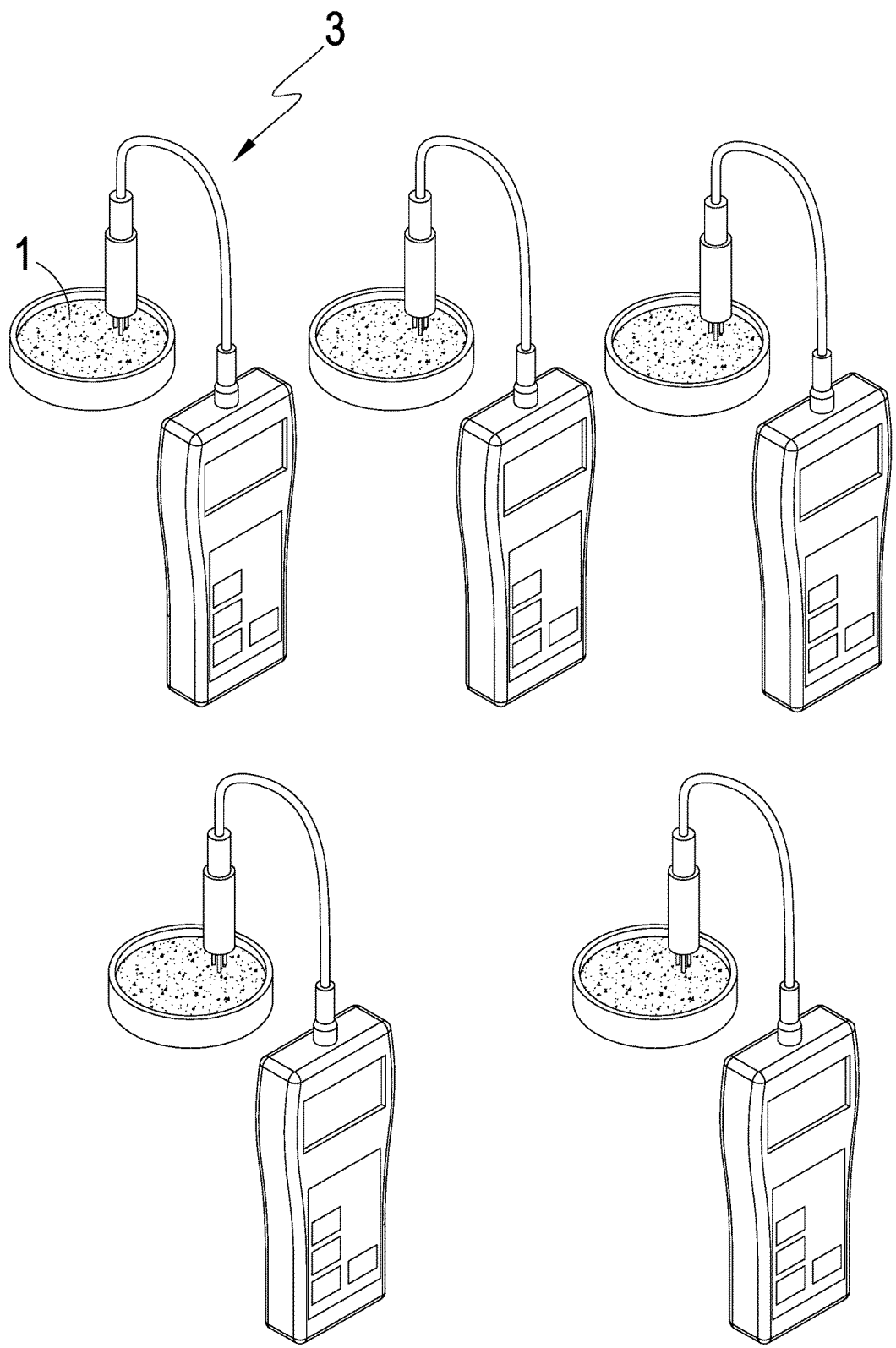
FIG. 3 is a schematic diagram showing how initial dielectric constants of soil samples are measured according to the method of FIG. 1.

In sub-step (a2), the training sample 1 is dried at 105 degree Celsius for 24 hours within an oven 2, as shown in FIG. 2. In sub-step (a3), as shown in FIG. 3, the initial electrical conductivity (EC(dS/m)) and the initial dielectric constant (K) of the training sample 1 are determined using a measurement device 3, such as a soil moisture meter.

Figure 4:
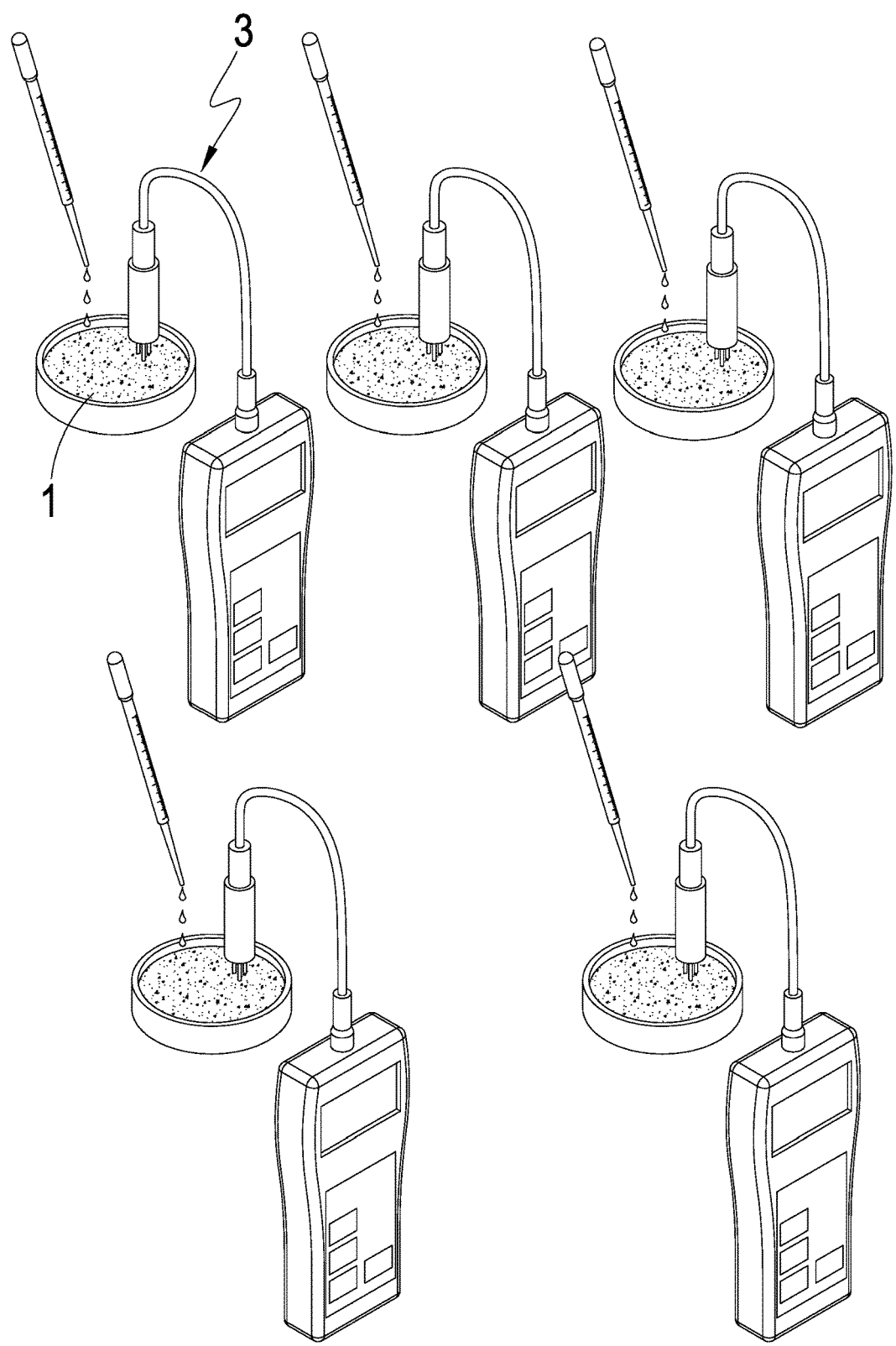
FIG. 4 is a schematic diagram showing how water is added to soil samples according to the method of FIG. 1.
Figure 5:
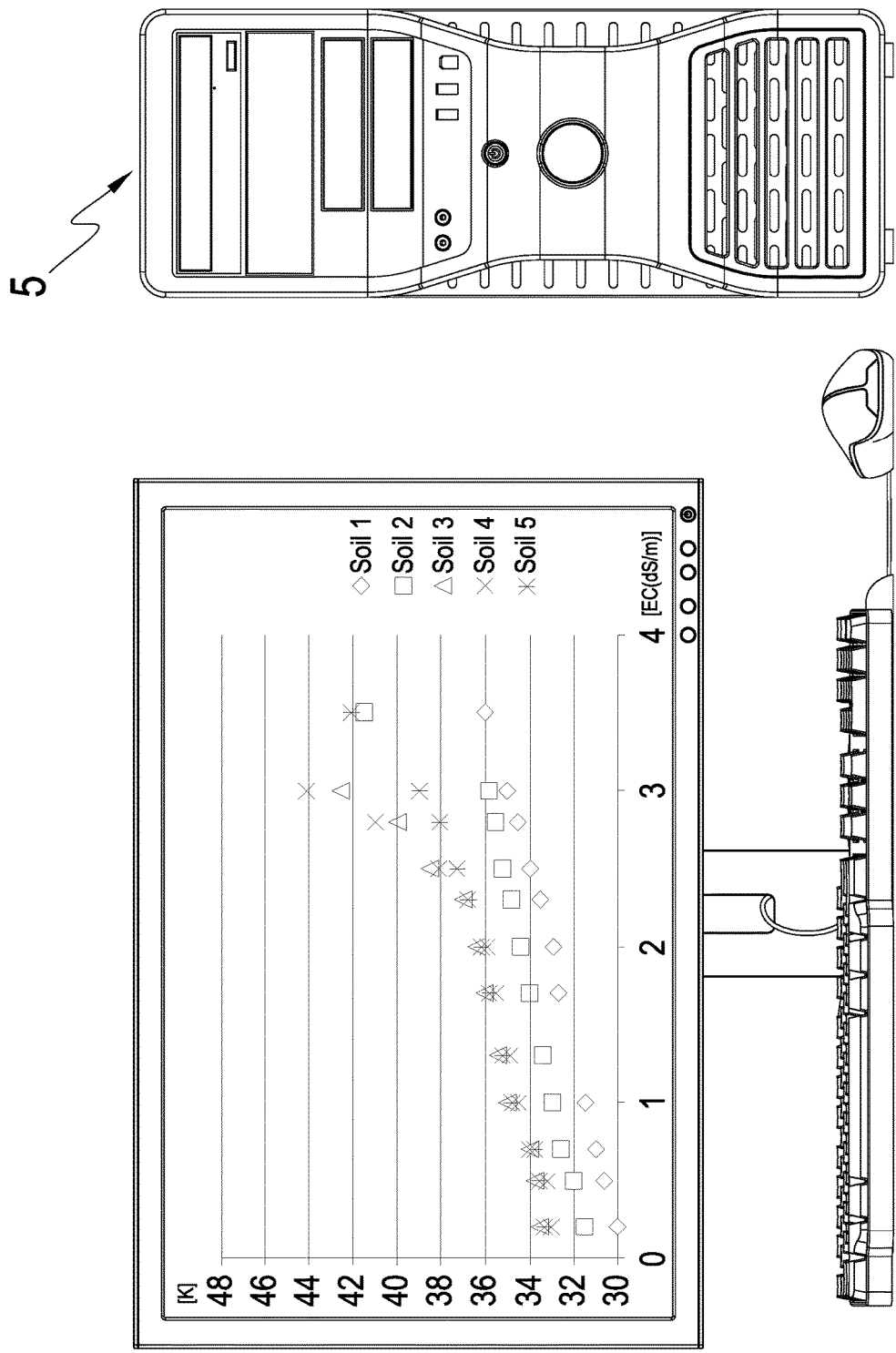
FIG. 5 is a schematic diagram showing measured electrical conductivities and dielectric constants displayed by a computing device according to the method of FIG. 1.
Figure 6:
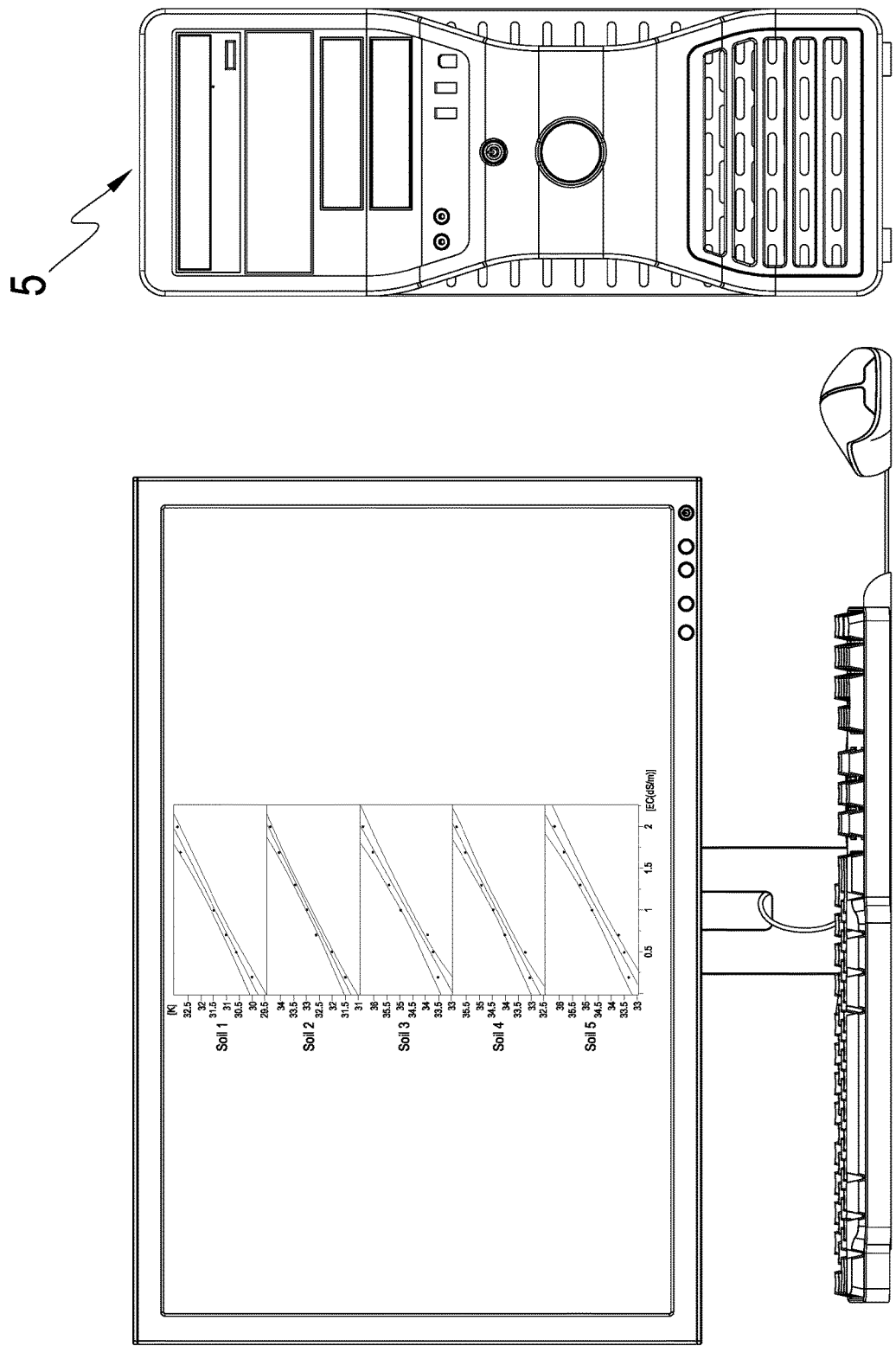
FIG. 6 is a schematic diagram showing how a regression value is obtained by a computing device according to the method of FIG. 1.

As shown in FIG. 4, in step (b), a fixed amount of water is added to the training sample 1 in several stages so that the humidity ratio is gradually increased, and a number of electrical conductivities and a second dielectric constant are determined using the measurement device 3 at each stage. As shown in FIG. 5, in step (c), the initial and subsequently obtained electrical conductivities and dielectric constants are entered into a computer device 5 such as a computer. As illustrated, it can be seen that, when electrical conductivity is higher, the dielectric constant is also higher. Then, as shown FIG. 6, step (d) obtains a regression value for data whose electrical conductivities are less than a threshold using the computing device 5. In the present embodiment, the threshold is 2 dS/m, and the regression values for the five training samples satisfy the following equations:

Soil1: $K=29.76+1.66\times EC$;

Soil2: $K=31.29+1.63\times EC$;

Soil3: $K=32.98+1.76\times EC$;

Soil4: $K=32.65+1.67\times EC$;

Soil5: $K=32.78+1.66\times EC$.

Therefore, taking training sample Soil1 as example, for its measured electrical conductivities below 2 dS/m, the regression value is (K−1.66×EC).

Figure 7:
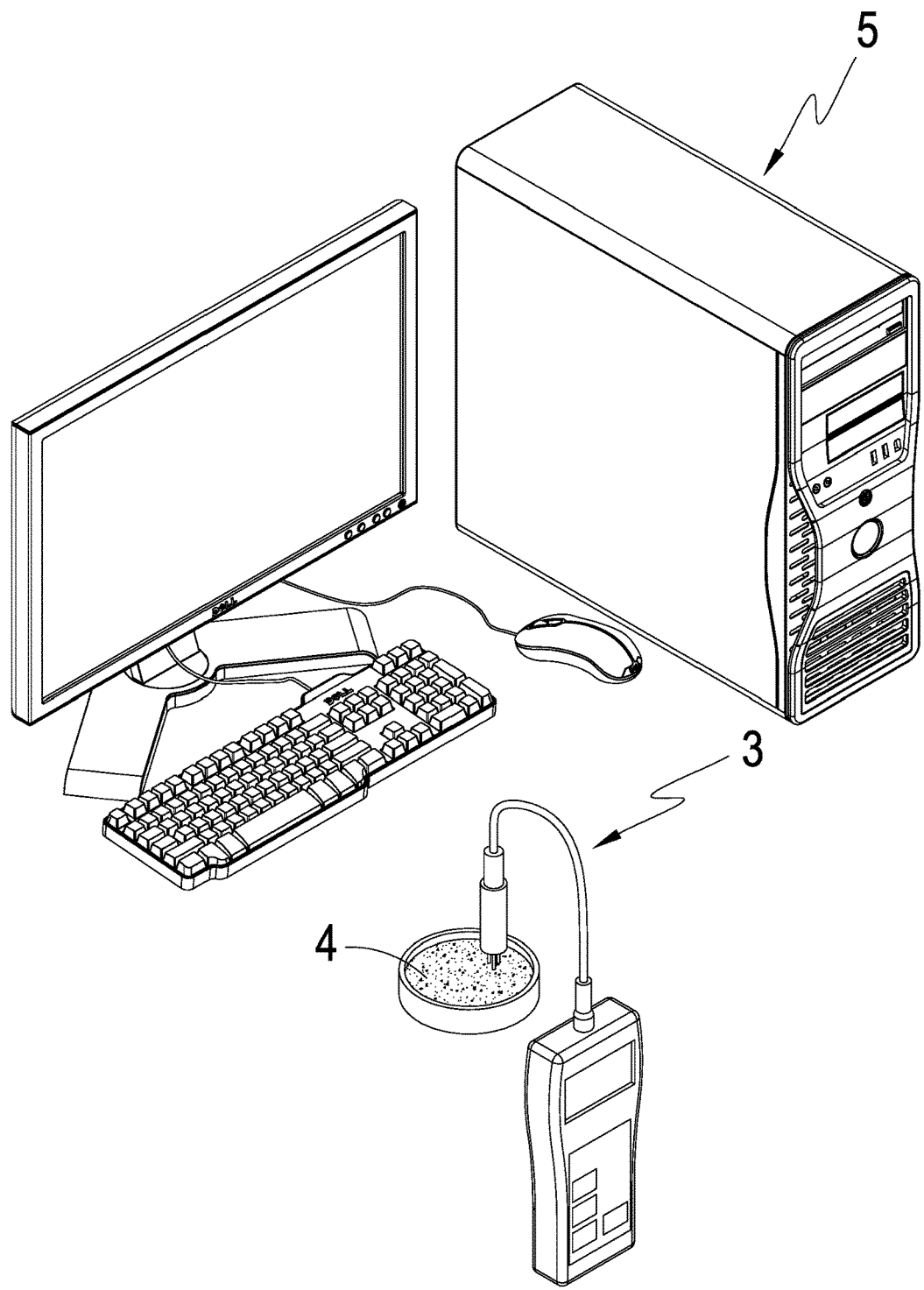
FIG. 7 is a schematic diagram showing the determination of soil moisture by a computing device according to the method of FIG. 1.
Figure 8:
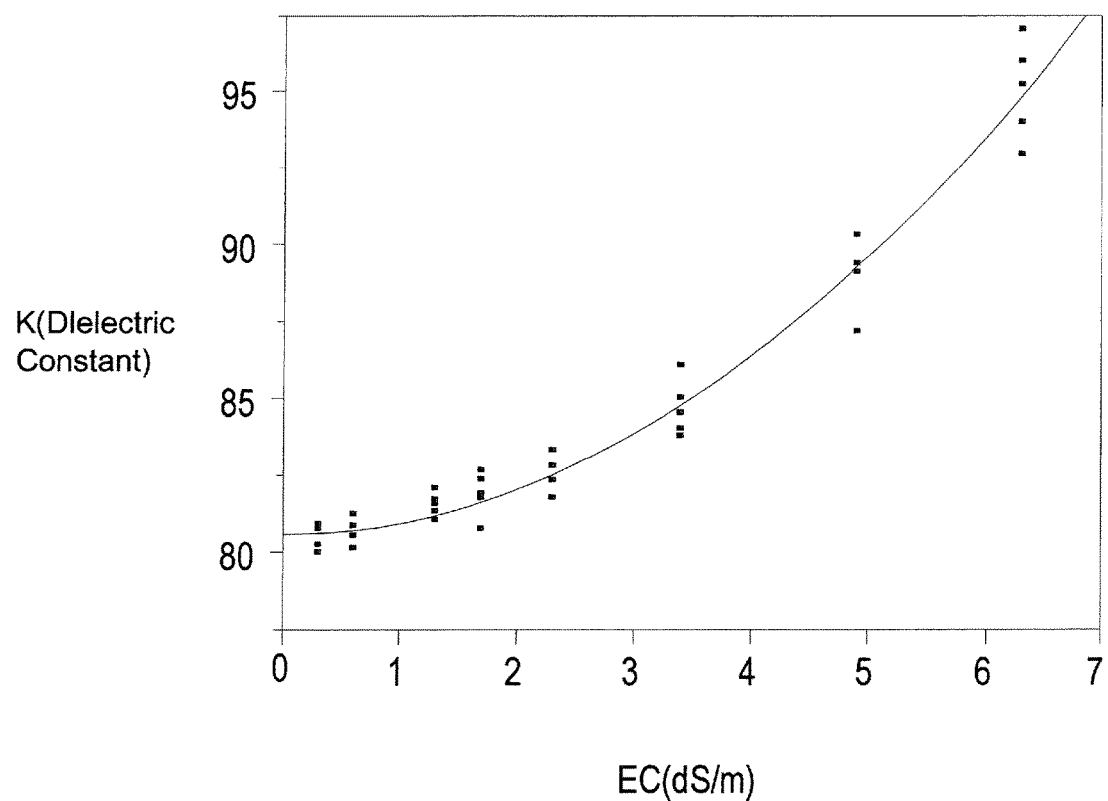
FIG. 8 is a diagram showing the relationship between electrical conductivities (ECs) and dielectric constants measured from eight soils.

As shown in FIG. 7, in step (e), a real sample 4 is obtained from the soil whose moisture is to be determined and its electrical conductivity and dielectric constant are measured using the measurement device 3. Then, in step (f), the soil moisture of the real sample 4 is determined based on the measured electrical conductivity and dielectric constant of the real sample 4 using the computing device 5. Taking the training sample Soil1 as example, its soil moisture is determined as $-5.3\times10^{-2}+2.92\times10^{-2}\times(K-1.66\times EC)-5.5\times10^{-4}\times(K-1.66\times EC)^2+4.3\times10^{-6}\times(K-1.66\times EC)^3$.

Subsequently, the composition of the training sample 1 and its corresponding regression value is recorded for future application.

Therefore, the gist of the present invention lies that a regression value is obtained using a training sample 1 and using the regression value, together with the real sample 4's measured electrical conductivity and dielectric, to determine an accurate soil moisture for the soil from which the real sample 4 is gathered.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A method for determining soil moisture, comprising
   (a) measuring an initial electrical conductivity and an initial dielectric constant of a training sample of a soil;
   (b) adjusting the training sample's water content by adding a fixed amount of water and obtaining a plurality of adjusted electrical conductivities and dielectric constants from the adjusted training sample;
   (c) entering the initial and adjusted electrical conductivities and dielectric constants into a computing device;
   (d) obtaining a regression value from the initial and adjusted electrical conductivities and dielectric constants of the training sample;

(e) measuring a final electrical conductivity and a final dielectric constant from a real sample of the soil; and (f) determining the soil moisture of the soil using the regression value and the final electrical conductivity and dielectric constant of the real sample.

2. The method according to claim 1, wherein the step (a) comprises (a1) obtaining a fixed volume of the soil as the training sample, (a2) drying the training sample at 105 degree Celsius for 24 hours within an oven, and (a3) measuring the initial electrical conductivity and the initial dielectric constant of the training sample using a measurement device.

3. The method according to claim 2, wherein the measurement device is a soil moisture meter.

4. The method according to claim 1, wherein the soil comprises at least one of sandy soil, loam, clay soil, peat soil, peat moss, organic cultural soil, coconut bran, peat, coconut peat, coconut soil, cultural soil for cuttage propagation, field soil, easy transplanting soil, coir soil, coir brick, and coconut fiber soil.

5. The method according to claim 1, wherein the fixed amount of water is added in a plurality of stages.

6. The method according to claim 1, wherein the regression value and the soil moisture are calculated by a computing device.

7. The method according to claim 1, wherein a composition of the training sample and its corresponding regression value is recorded for future application.

* * * * *